(12) United States Patent
Shvets et al.

(10) Patent No.: US 9,091,670 B2
(45) Date of Patent: Jul. 28, 2015

(54) CLEANING OF SYSTEM FOR DISPENSING OF LIQUID DROPLETS

(75) Inventors: Igor Shvets, Dublin (IE); Cecilia Franken, Dublin (IE); Aoife Gallagher, Dublin (IE); Jeurgen Osing, Dublin (IE)

(73) Assignee: Allegro Research Limited, Dublin (IE)

( * ) Notice: Subject to any disclaimer, the term of this patent is extended or adjusted under 35 U.S.C. 154(b) by 1138 days.

(21) Appl. No.: 13/019,212

(22) Filed: Feb. 1, 2011

(65) Prior Publication Data

US 2012/0024888 A1 Feb. 2, 2012

Related U.S. Application Data

(63) Continuation of application No. 11/409,485, filed on Apr. 24, 2006, now abandoned.

(30) Foreign Application Priority Data

Apr. 22, 2005 (IE) .................................. S2005/0243

(51) Int. Cl.
| | |
|---|---|
| *G01N 1/10* | (2006.01) |
| *G01N 1/14* | (2006.01) |
| *G01N 35/10* | (2006.01) |
| *B01L 99/00* | (2010.01) |
| *B01L 3/02* | (2006.01) |

(52) U.S. Cl.
CPC ............ *G01N 35/1004* (2013.01); *B01L 99/00* (2013.01); *B01L 3/021* (2013.01); *Y10T 436/114998* (2015.01)

(58) Field of Classification Search
CPC ............. G01N 1/02; G01N 1/10; G01N 1/14; B01L 3/0217; B01L 3/0234; B01L 3/0241; B01L 2400/06

USPC ................... 436/180, 49, 52, 55, 43, 54; 422/62–68.1, 500–570

See application file for complete search history.

(56) References Cited

U.S. PATENT DOCUMENTS

| | | | |
|---|---|---|---|
| 4,574,850 A | 3/1986 | Davis | |
| 5,035,150 A | 7/1991 | Tompkins | |
| 5,341,691 A | 8/1994 | Callis et al. | |
| 5,396,812 A | 3/1995 | Peterson | |
| 5,474,796 A | 12/1995 | Brennan | |
| 5,743,960 A | 4/1998 | Tisone | |
| 5,744,099 A | 4/1998 | Chase et al. | |
| 6,063,339 A * | 5/2000 | Tisone et al. | 422/67 |
| 6,079,283 A | 6/2000 | Papen et al. | |
| 6,322,752 B1 * | 11/2001 | Siddiqui et al. | 422/510 |
| 6,511,849 B1 | 1/2003 | Wang | |
| 6,627,157 B1 | 9/2003 | Doktycz et al. | |
| 6,669,909 B2 | 12/2003 | Shvets et al. | |
| 6,692,703 B2 * | 2/2004 | Shoji et al. | 422/527 |
| 6,692,968 B2 * | 2/2004 | Burshteyn et al. | 436/63 |
| 6,713,021 B1 | 3/2004 | Shvets et al. | |
| 6,773,673 B1 * | 8/2004 | Layfield et al. | 422/81 |
| 2003/0170903 A1 | 9/2003 | Johnson et al. | |

FOREIGN PATENT DOCUMENTS

WO WO 99/42752 8/1999

* cited by examiner

*Primary Examiner* — Brian R Gordon
(74) *Attorney, Agent, or Firm* — Jones Day

(57) ABSTRACT

There is provided a method of cleaning a dispensing assembly for small liquid droplets less than 50 µl and even as low as 10 nl. A purging step with pressurized gas followed by a cleaning step using a suitable cleaning liquid is carried out a number of times.

9 Claims, 4 Drawing Sheets

CLEANING OF SYSTEM FOR DISPENSING OF LIQUID DROPLETS

This application is a continuation of U.S. patent application Ser. No. 11/409,485, filed Apr. 24, 2006, now abandoned, which claims priority to Irish Application No. S2005/0243, filed Apr. 22, 2005, both applications being incorporated by reference herein for all purposes.

INTRODUCTION

The present invention relates to the cleaning, operation and construction of a dispensing assembly for liquid droplets of the order of 50 µl in volume and as low as 10 nl ($10^{-8}$ l) or even smaller. Further the invention is directed towards providing a method for dispensing such droplets with reduced carryover, namely, the leaving of traces of a sample liquid in a dispenser after the dispenser has been emptied which then mix with the future sample liquids. Further, the invention provides a method and apparatus for cleaning a low volume dispensing system and a dispensing system including a cleaning system.

PRIOR ART

The present invention relates to an assembly for dispensing and aspirating small volumes of liquid as used extensively for drug development in the pharmaceutical industry, and also in medical diagnostics, biotechnology and indeed small droplets of liquids as used for many techniques in industry. Particular examples of this are High Throughput Screening (HTS), Polymerase Chain Reaction (PCR), combinatorial chemistry, DNA sequencing, genotyping, microarraying and proteomics, although obviously not limited to those. The invention is also directed towards the aspiration of liquids from sample wells so that the liquid can be transported between wells. In many applications related to life science areas the liquids are stored, mixed and reacted in well plates or so-called micro-titre plates.

Transfer of liquid from and into well plates is common. The invention has as an objective its utilisation with micro-titre plates although its use is not limited to these. In some of the applications, the well plates are designed in a particular way so that each well is further segmented into a number of sections. This is the case e.g. in protein crystallography where each well is sectioned into three segments or more so that they could contain different liquids. It is an objective that the invention can also be utilized with such specialised micro-titre plates. In some other applications the arrays of liquids are created on flat glass or polymer substrates. For example, such flat substrates are used in the applications known as DNA and protein arrays. The invention can also be used for these applications. In some other applications the liquids are stored in vials or transferred between the vials, and again the invention can be used to transfer liquids between containers of this type. Yet in many other applications the liquids are stored and moved between containers and substrates of at least two different kinds, e.g. flat substrates and well plates, or between well plates and vials, etc. Again the invention is directed to use for such transfer of liquids to, from and between these unlike containers and substrates.

Development of instrumentation for dispensing of minute volumes of liquids has been an important area of technological activity for some time. Numerous devices for controlled dispensing of small quantities of liquids with the volume of 1 µl and below, have been developed over the past twenty five years. These are used e.g. for various printing applications, in the electronics industry for making printed circuit board (application of fluxes, etc.) in precision mechanics (application of lubricants, etc.). More recently a wide range of new areas of applications has emerged for devices handling liquids in the low microliter range, in particular in the area of life sciences.

The requirements of a dispensing system vary significantly depending on the application. For example, the main requirement of a dispensing system for ink jet applications is to deliver droplets of a fixed volume with a high repetition rate. The separation between the individual nozzles should be as small as possible so that many nozzles can be accommodated on a single printing cartridge. On the other hand in this application the task is simplified by the fact that the mechanical properties of the liquid dispensed, namely the ink are well defined and consistent. Also in most cases the device used in ink jet applications does not need to aspirate the liquid through the nozzle for the cartridge refill.

For most applications in life sciences and medicine the requirements imposed on a dispensing system are completely different. For example, in the HTS applications, the system should be capable of handling a variety of reagents with different mechanical properties, e.g. viscosity. Often these systems should be also capable of aspirating the liquids through the nozzle from a well. On the other hand there is not such a demanding requirement for the high repetition rate of drops as in ink jet applications. Another common requirement in many life science applications is that carryover between different wells served by the same dispensing device be avoided as much as possible.

The severity of this particular requirement depends on the specific application. For example in the DNA sequencing and genotyping typically the level of the acceptable carryover is very low. In the HTS applications the requirement for the carryover is often rather stringent. In certain applications related to medical diagnostics any contamination is virtually unacceptable at least for the reasons of legal liability associated with the outcome of the medical test if not for other practical reasons.

Carryover arises because the dispenser aspirates and dispenses various sample liquids in sequence one after another. As the traces of liquids remain in the system after the dispensing, this leads to carryover. Usually the most common way to avoid carryover is to completely empty the system of one sample liquid and then wash it with washing liquid before aspirating the next sample liquid. As one would expect, a more thorough wash cycle is also more time consuming. Therefore the requirement for the reduced carryover is balanced against the productivity of the dispensing station (number of liquids handled per hour).

For many applications, the dispensing method must be non-contact, i.e. the dispensing nozzle during the dispensing should not be in contact with the substrate. Some non-contact dispensing techniques rely on a positive displacement pump such as described in the U.S. Pat. No. 5,744,099 (Chase et al.). The pump consists of a syringe with a plunger driven by a motor, usually a stepper or servo-motor. The syringe is usually connected to the nozzle of the liquid handling system by means of flexible polymer tubing. The nozzle is typically attached to the arm of a robotic system which carries it between different wells for aspiring and dispensing the liquids. The syringe is filled with system liquid such as water. The system liquid continuously extends through the flexible tubing into the nozzle towards the tip. The liquid reagent that needs to be dispensed (hereinafter called sample liquid), fills up into the nozzle from the tip. In order to avoid mixing of the system liquid and the sample liquid and therefore reduce carryover, an air bubble or bubble of another gas is usually positioned between them. As described in detail in patent specifications U.S. Pat. No. 6,669,909 (Shvets et al) and U.S. Pat. No. 6,713,021 (Shvets et al), the compressibility of the gas bubble between the sample liquid and the system liquid is a significant source of error. Similarly the problems of dispensing drops of small volume are also described and discussed in U.S. Pat. No. 4,574,850 (Davis) and U.S. Pat. No. 5,035,150 (Tompkins). Dispensing of droplets of small volumes by a pressure pulse across a well defined air bubble separating the system liquid and the sample liquid is also described in detail in U.S. Patent Application Publication No. 2003/0170903 (Johnson et al.) filed in 2003. It should be pointed out that a small air bubble cannot reliably prevent mixing of the sample liquid and the system liquid. The reason is that during the dispensing and the aspiration the liquids and the air bubble move within the tubing. If the air bubble is too small then during rapid movement of the liquids there is chance of them intermixing. On the other hand the larger the air bubble, the more is the accuracy of the dispensing compromised as its compressibility increases with the volume of the air bubble. For low volume liquid dispensing one could typically set the volume of the air bubble at the level of some 1-5 μl, but smaller bubbles in practice cannot prevent intermixing of the system liquid and the sample liquid. It should be noted that even relatively large air bubbles cannot completely prevent carryover. The mechanism of carryover in this case is as follows: during the dispensing the proximal end of the sample liquid pushes along the tubing towards the nozzle. Some quantity of the sample liquid then adheres to the walls of the tubing. As the following system liquid advances along the tubing, this is washed away from the tubing and absorbed into the system liquid. Then during the next aspiration cycle the distal end of the system liquid is retracted along the tubing leaving some traces of it on the walls and the new sample liquid advances into the tubing washing away and absorbing the traces of the previous sample liquid.

In order to completely avoid carryover, disposable tips are used in certain applications so that the part of the dispenser that comes in contact with the sample liquid is discarded after each aspirate-dispense cycle. There are certain disadvantages associated with this approach as well.

Some methods of non-contact dispensing rely on a magnetic valve attached to the distal end of a conduit, typically a solenoid valve. For aspiration of the liquid the proximal end of the conduit is connected to a vacuum source that creates negative pressure in the line. For dispensing the proximal end of the conduit is connected to the pressure source that creates positive pressure within the conduit and therefore the sample liquid is ejected from it.

For low volume dispensing these methods utilising the solenoid valve have many advantages over the methods based on a positive displacement pump. However, there are also further potential complications in relation to carryover. The reason is that a solenoid valve is normally not used as a disposable element due to its high cost. Therefore, the contaminated chamber of the valve needs to be washed thoroughly to reduce carryover. Furthermore, the fluid path in the valve is usually torturous; the valve contains a number of parts and pockets where the contamination can build up complicating the cleaning procedure.

Various attempts in the past have been made to address the problem of such conventional solenoid valves. A typical example of these is the invention described in the PCT Patent Specification No WO 99/42752 (Labudde). This patent specification discusses the problems associated with using conventional solenoid valves for many applications in low volume dispensing in life sciences. The solution proposed in WO 99/42752 (Labudde) is to design a "non torturous" flow path for the liquid in the valve. In this patent specification, the effect of the use of a blunt or rounded valve seat is discussed as well as the effect of the of the area of the valve seat orifice opening.

U.S. Pat. No. 6,669,909 (Shvets et al) and U.S. Pat. No. 6,713,021 (Shvets et al) describe other methods of dispensing. These methods use a floating boss valve installed at the end of the conduit that can be pressurised for dispensing or pumped out for aspiration. The design of this valve is such that the flow path for the liquid is straightened and the number of pockets where the residues of the sample liquid can be accumulated is reduced. This type of valve has other advantages over the solenoid valve from the point of accuracy and reproducibility of low volume dispensing.

U.S. Pat. No. 5,743,960 (Tisone) describes another method of dispensing submicroliter volumes of fluids for life science applications. This method combines a positive displacement pump and a conventional solenoid valve. The positive displacement pump is a syringe pump filled with a fluid to be dispensed. The pump is connected to tubing at the other end of which there is a solenoid valve located close to the ejection nozzle. The dispensing volume and the repetition rate of the drop dispensation are determined by the rate of expulsion of the liquid from the syringe pump and the frequency of the valve open-close switching. This method is particularly suitable for the dispensing of a large number of identical droplets. This method is further described in U.S. Pat. No. 6,063,339 (Tisone) teaching how to set the correct timing of the valve of opening pulses in order to achieve desired patterns on substrates. Another method described in the U.S. Pat. No. 6,079,283 (Papen) utilises the syringe pump and the piezo actuator.

Another method was proposed in U.S. Pat. No. 6,627,157 (Doktycz). This invention is aimed at making arrays of biological liquids: large number of identical drops of the same liquid. In many non-contact dispensers for making arrays, the sample liquid is fed into the dispenser from the back, from a special bottle filled with it. U.S. Pat. No. 6,627,157 (Doktycz) also utilises such approach. Further in the invention there are four conduits coupled to a switching valve: one leading to the nozzle for the sample ejection, the second one filled with the sample liquid connected to the bottle/container containing the sample liquid, the third conduit contains the liquid for purging the dispenser and the fourth line is connected to a pressure source. During the operation the switching valve is first set to the position linking the sample liquid to the nozzle. Then the valve position is changed coupling the nozzle to the ejection line. In this way the sample liquid is ejected from the nozzle.

It will be appreciated by those skilled in the art that all these methods must deal with the issue of carryover. The most typical way of cleaning the dispenser is based on aspirating cleaning liquid into the nozzle of the tip from a reservoir of the cleaning liquid and then dispensing it back into the reservoir. The more stringent is the requirement for the low carryover, the greater is the number of cycles of the aspiration and dispensing of the cleaning liquid required. The greater number of aspiration-dispensing operations of the cleaning liquid after each change of the sample liquid implies reduced productivity of the dispenser. In some methods utilised for making the array of identical dots of the same material, for cleaning the system the bottle with the biological liquids dispensed is replaced by a bottle of cleaning solution. Such a bottle is connected at the distal end of the conduit remote from the nozzle. The solution is pumped through the dispenser. This is proposed e.g. in U.S. Pat. No. 6,511,849 (Wang). The problem with this approach is that it is not clear how this could be utilised in the dispensers that also work in the aspirate mode, i.e. the dispensers that aspire liquid though the nozzle. In the case of aspiration of the sample liquid through the nozzle, the cleaning liquid would mix with the sample liquid disrupting the entire process of dispensing.

OBJECTS OF THE INVENTION

It is an objective to provide a method and system for cleaning a dispenser which dispenses at a volume of 100 μl and below. The present invention is directed towards the provision of a low volume dispensing system that could minimise carryover and yet could operate with relatively short washing cycle so that the productivity of the instrument is enhanced. It would be further advantageous to have such instrument capable of operating in the aspirate-dispense mode so that the sample liquid is collected through the nozzle of the instrument.

The objective of the present invention is to provide a dispensing device that can operate with reduced carryover in low volume liquid dispensing at the volume of 100 μl and below. It is the further objective to provide a dispensing device that is capable of operating in the aspirate-dispense mode so that the sample liquid is collected through the nozzle of the instrument and which operates with reduced carryover. The second objective is to provide a device and method for minimising the washing time of a dispensing device so that the productivity of the instrument is enhanced.

SUMMARY OF THE INVENTION

The present invention provides a method of cleaning a dispensing assembly for small liquid droplets of up to 100 μl in volume. It is particularly directed towards those dispensers for droplets of 10 μl or less. Portion of these dispensers can be contaminated by a liquid used in the dispenser, whether it be sample liquid or system liquid or a mixture of both where a dispensing assembly uses system liquid.

The method comprises the purging step of delivering pressurised gas such as air through the contaminable portion of the dispenser to expel liquid and fill with the purging gas, and then a cleaning step is carried out of delivering pressurised cleaning liquid through the contaminable portion to flush it.

Generally the purging step is carried out before the cleaning step and indeed a purging step usually forms the final step. Further, in accordance with a method of the invention, in either or both of the cleaning step and the purging step, the flow of liquid or gas is cut off and then started again so as to give a pulse flow which helps in the scouring of the contaminable portion of the dispenser. An initial evacuation step may be carried out which while it can in some circumstances lead to contaminants being drawn further into the assembly it gets rid of air pockets and hence leads to better cleaning. Usually the purging and cleaning steps will be carried out at least twice and more generally, four or five times. Various purging gases may be used such as air, helium, nitrogen, carbon dioxide and any other gas that will not contaminate the sample liquid.

Various pressure sources for both air pressure and liquid pressure may be provided and valving may be used to provide the desired effect.

Further, there is provided, with the apparatus for carrying out the method, a dispenser in which there is an additional drug sample line that can be connected into the system so as to deliver one particular liquid to a considerable number of different sample liquids such as, for example, a buffer liquid which might be required to dilute samples. Then, the buffer liquid would be dispensed from the bulk sample container to a bulk sample line.

DETAILED DESCRIPTION OF THE PREFERRED EMBODIMENTS

Figure 1:
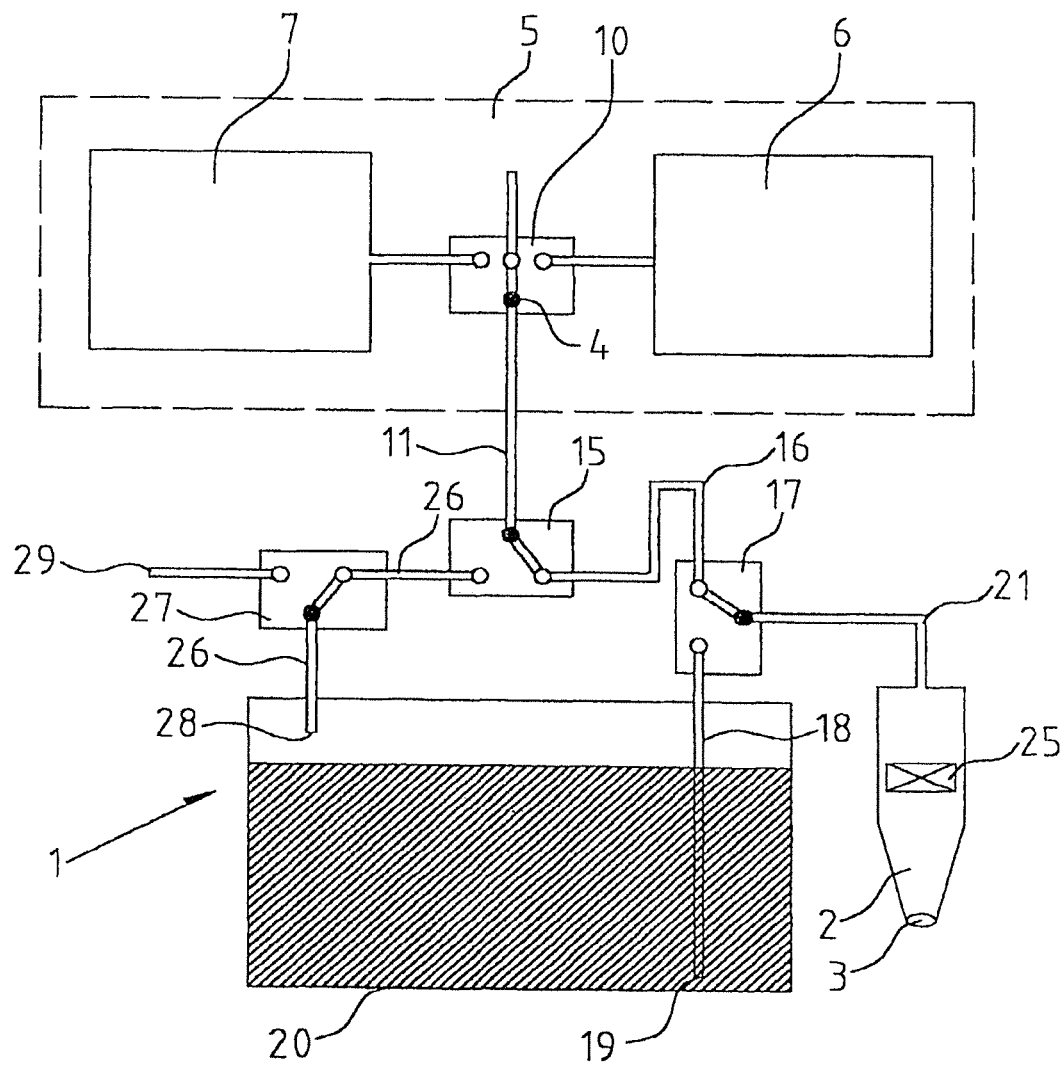
FIG. 1 illustrates diagrammatically the system for dispensing and aspiration of low volumes of liquids incorporating the invention.

FIG. 1 shows a dispensing assembly for dispensing and aspiration of low volumes of liquids, indicated generally by the reference numeral 1, hereinafter, for brevity, the system 1. The system 1 has a dispensing tip 2 terminating in a nozzle 3 that can be connected to an output 4 of a pneumatic source 5 delineated by interrupted lines. The pneumatic source 5 comprises a pressure source 6 and a vacuum source 7 provided by a compressor, not shown. The pneumatic source 5 connects the pressure source 6 and vacuum source 7 via a switching valve 10 to a conduit The conduit 11 in turn feeds, via a switching valve 15, a pneumatic line 16 which in turn feeds a valve 17. The valve 17 is connected to a liquid feed line 18 terminating at an inlet 19 mounted in a cleaning liquid tank or flush bottle 20. The valve 17 also feeds a pneumatic line 21 connected to the dispensing tip 2.

The dispensing tip 2 houses a valve 25. The valve 15 is also connected to a further pressurising line 26 housing a valve 27 and terminating in an outlet 28. Therefore, the pneumatic line 16 can be connected either to the pressurising line 26 or to the conduit 11. Further the flush bottle 20 is connected to the pressurising line 26 so that the inlet 28 of the pressurising line 26 is connected to the flush bottle 20 and the inlet 19 of the liquid feed line 18 is connected to the flush bottle 20 below the level of cleaning liquid, i.e. the level of cleaning liquid in the flush bottle 20. The outlet 28 of the pressurising line 26 could be connected to the flush bottle 20 either above or below the level of cleaning liquid in the flush bottle 20. Both the inlet 19 of the liquid line 18 and the outlet 28 of the pressurising line 26 are connected to the flush bottle 20 in an air tight fashion so that the flush bottle 20 can be pressurised by the pneumatic source 5. It may be beneficial to have the valves 15 and 17 such that the segment of the pneumatic line 16 and the segment of the pressurising line 26 remain air tight, i.e. the interiors of the lines are not open to air at any position of the valves 15 and 17. For example, if the excess pressure is set in the flush bottle 20 and the valves 15 and 17 are set to the upper positions, then the flush bottle 20 still remains under pressure so that the two ends of the liquid feed line 18 and pressurising line 26 are sealed. This kind of valve is well known to people skilled in the art. It will be appreciated by those skilled in the art that any of the three way valves or two-ways switching valves described in the specification could in fact be composed of a set of simple two-way blocking solenoid valves all controlled by the same controller.

In this particular embodiment, as stated above, the dispensing tip 2 also has the valve 25 separating the nozzle 3 of the dispensing tip 2 and the pneumatic line 21. Preferably the valve 25 is installed close to the nozzle 3 of the dispensing tip 2. The valve 25 could be e.g. a floating boss valve similar to the one described in the U.S. Pat. No. 6,669,909 (Shvets et al) and U.S. Pat. No. 6,713,021 (Shvets et al). Alternatively it could be a regular solenoid valve.

The pneumatic source 5, as described above, comprises two sources, namely the pressure source 6 and the vacuum source 7. In a typical embodiment the vacuum source 7 and the pressure source 6 are two air tight containers with an internal volume of some 0.1-1/each connected to the low pressure and high pressure ends of a compressor respectively. A suitable compressor is the miniature compressor O/N NPK09DC (KNF Neuberger). Typically the pressure in the vacuum source is in the range from 0 mB to 800 mB below atmospheric pressure and the pressure in the pressure source is in the range of 0 to 5000 mB above the atmospheric pressure although values outside this range can also be used. In a typical embodiment the valves are controlled by processors via electronic controls which are capable of switching the valves independently of each other. These are not shown in FIG. 1 for simplicity as they are well known to those skilled in the art.

Operation of the system is as follows. For simplicity and ease of understanding, as the valves are illustrated diagrammatically, the settings of the valves are described by the illustrated position (left/right/up and down) as this more easily describes the operation than any other way. The switching valve 10 connects the vacuum source 7 to the output of the pneumatic source 5 by being positioned to the left. Then the valves 15 and 17 are set to the right position and upper position respectively as indeed shown in FIG. 1 so that the nozzle 3 is connected to the output 4 of the pneumatic source 5 via the conduit 11 and pneumatic lines, 16 and 21. Then the nozzle 3 is immersed in the sample liquid and the valve 25 is opened to aspirate the sample liquid into the dispensing tip 2. After that the pressure source 6 is connected to the output of the pneumatic source 5 by means of the valve 10 and excess pressure is set in the conduit 11 and the pneumatic lines 16 and 21. At the same time the vacuum source 7 is disconnected from the output of the pneumatic source 5. By opening the valve 25, the dispensing is achieved as the sample liquid is ejected from the dispensing tip 2 under the influence of the excess pressure. Once the dispensing tip 2 is empty of the sample liquid, the tip 2 is cleaned to reduce carryover as follows. The valves 15 and 17 are set to the left position and lower position respectively so that the dispensing tip 2 is connected to the output of the pneumatic source 5 via the liquid line 18 and pressurising line 26. The valve 25 is open and the cleaning liquid flows from the flush bottle 20 through the dispensing tip 2 towards the nozzle 3. The cleaning liquid flows towards the dispensing tip 2 under the influence of pressure set in the flush bottle 20 by the pneumatic source 5.

An alternative cleaning procedure may be employed. For example, where there is one or indeed a multiple of dispensing tips 2, the dispensing tip or tips may be connected by means of the pneumatic lines to the vacuum source and evacuated of gas. This is done by switching the valves 10, 15, 17 and 27. The reason for this is that if the dispensing tip is not evacuated prior to being filled with the cleaning liquid, the pockets of air or gas can remain in it preventing the cleaning liquid from reaching some areas within the dispensing tip. Once the tip is evacuated the pressure source 6 is connected to the flush bottle 20 containing the cleaning liquid and thus pressurising it. This is done by switching the valves 10, 15 and 27. Then the dispensing tip or tips 2 are connected to the liquid line 21 by switching the valve 17 and allowing the pressurised cleaning liquid to flow through the liquid line and fill up the dispensing tips 2. Then the pneumatic line 16 is pressurised by switching the valves 10 and 15. This step is optional but highly desirable. It is beneficial to prevent the back stream of liquid from the dispensing tip 2 and thus to prevent the contamination from coming into the pneumatic lines. Then the dispensing tips 2 are connected to the pneumatic line 16 by switching the valves 15 and 17 and activated a few times between the open and closed positions until at least the dispensing tips 2 are empty from the residual wash-sample liquid. In some cases, the valve 25 in dispensing tip 2 may be activated only once to the open position to empty the dispensing tip 2. The entire cycle then may be repeated a number of times until the dispensing tips 2 are clean. The benefit of this procedure is clear from the FIGS. 2 and 3.

Figure 2:
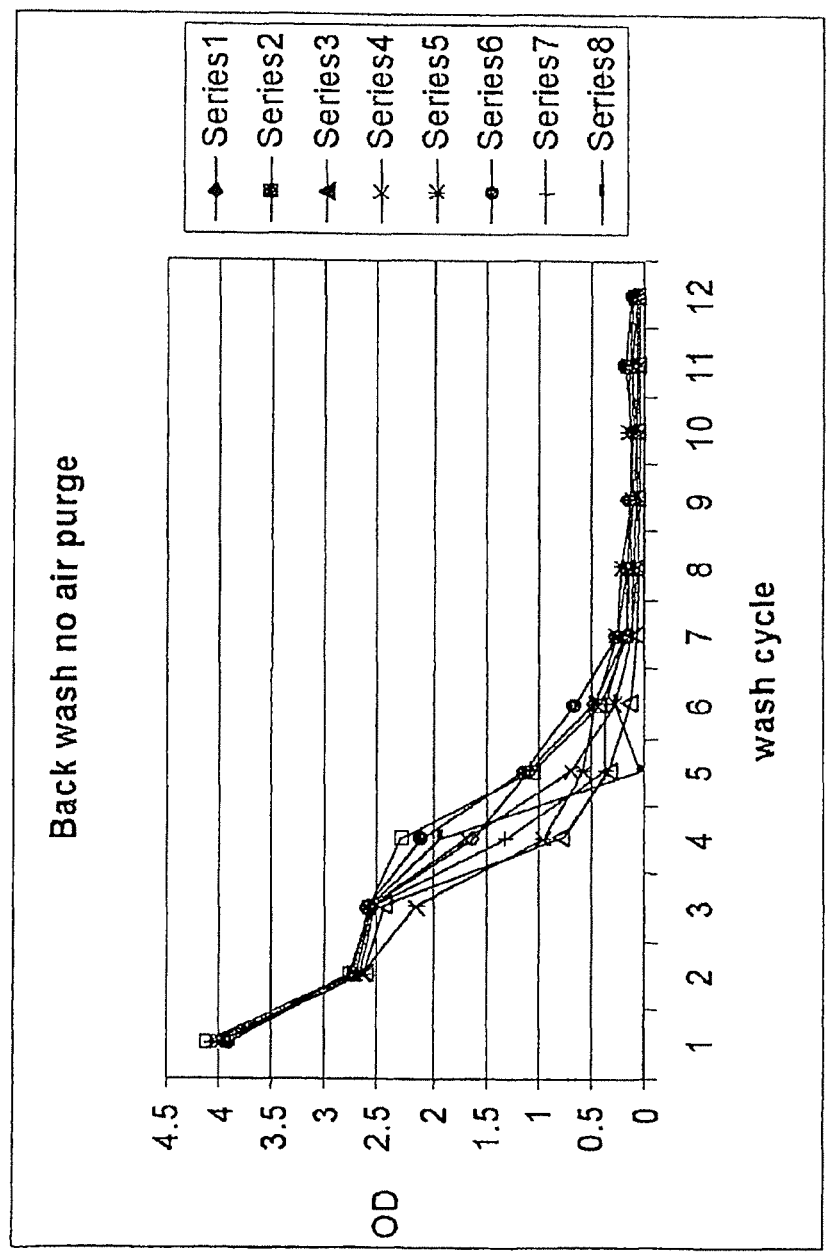
FIG. 2 shows the value of carryover according to a prior art cleaning procedure described.

FIG. 2 shows the contamination as a function of the volume of cleaning liquid dispensed through the dispensing tip. The conditions of the experiment were as follows:

The tip used as part of this dispense mechanism in these experiments is based on the SPOT ON™ technology described in U.S. Pat. No. 6,669,909 (Shvets et al) and U.S. Pat. No. 6,713,021 (Shvets et al). The dispensing tip is made up of four components: tip body, end plug, capillary tube and magnet. The total length of the tip body is 39.5 mm. The inner diameter (ID) of the lower section (magnet chamber) of the tip is 2.44 mm. There are 8 guiding rails in this chamber for aligning the magnet. The outer diameter (OD) of the upper section is 6.35 mm±0.01 mm. The material of the tip body used is PEEK 450G. The lower assembly is made up of the end plug and the stainless steel capillary tube. The capillary is inserted into the mould and the end plug is formed around it. The capillary is made from grade 304 stainless steel and is gauge 30. The nominal ID of the capillary is 0.16 mm. The nominal OD of the capillary is 0.31 mm. The magnet is cylindrical with dimensions 0.07" diameter×0.275" long and made from Samarium Cobalt permanent magnetic material. The magnet is coated on all surfaces except the North Pole face with parylene 'C' to a thickness of 25 um. Silicon adhesive rubber of 300 um thickness approx is deposited on the North Pole face and cured. No air purging was applied in the cleaning procedure presented in FIG. 2.

In the experiments described here the tips were used to dispense 10% w/w fluorescein sodium salt in water. To detect the rate of cleaning of this fluorescent compound from the tips, water was flushed through using the described invention. 120 µl aliquots of this wash liquid was collected in optical bottomed 96 well plates. Up to 12 aliquots were collected and analysed. The amount of fluorescent compound remaining was discerned by reading the plates in a spectrophotometer (plate reader) at a wavelength of 495 nm. The well plate reader used was a Biotek Power Wave HT.

Figure 3:
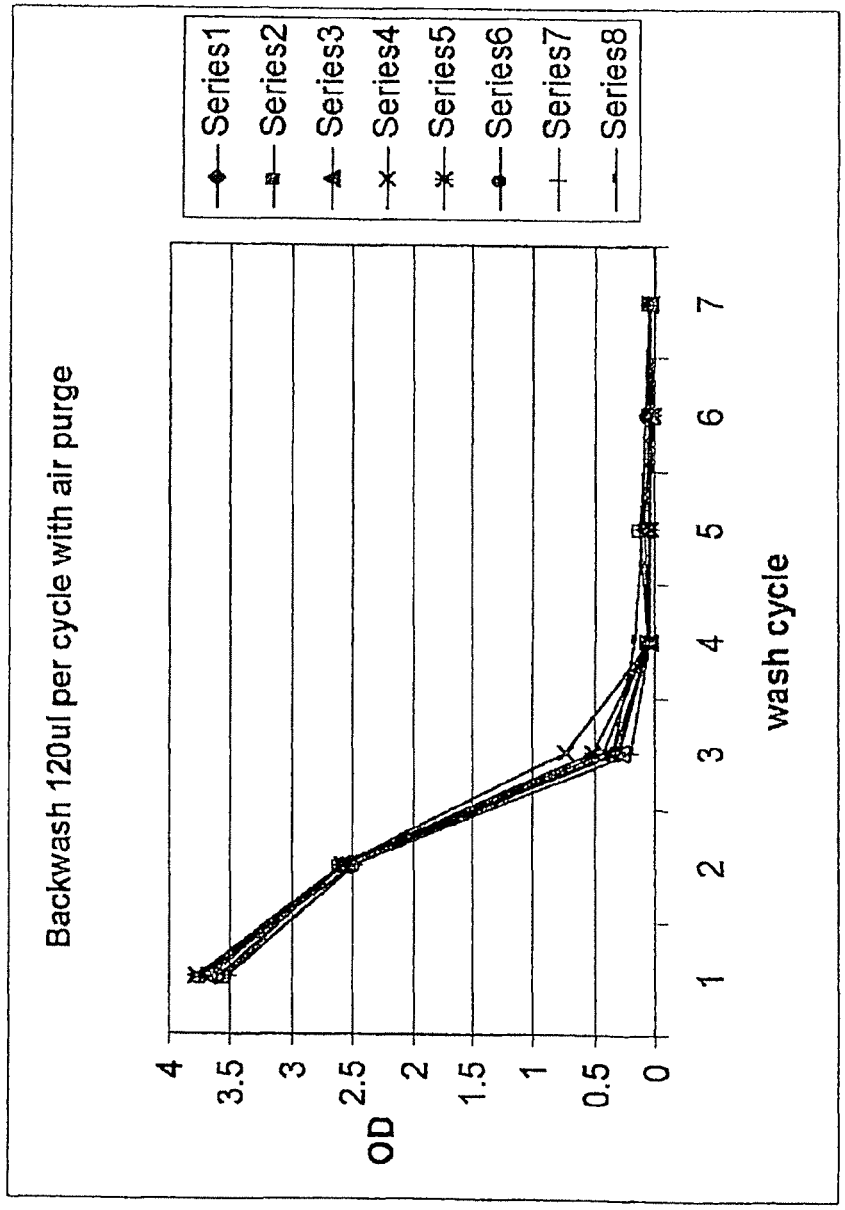
FIG. 3 shows the value of carryover according to a cleaning procedure in accordance with the invention described.

FIG. 3 shows the contamination level when the cleaning procedure was altered so that the dispensing tip is periodically purged of the cleaning liquid by air as described above with reference to FIG. 1. In this experiment each cleaning cycle consisted of flushing of 120 µl of cleaning liquid through the tip followed by purging the tip with air. In each cycle the valves 15 and 17 were actuated to switch the connection of the dispensing tip 2 to the pneumatic source 5 either via the pneumatic line 16 or via the liquid line 18 as described above. The amount of air blown though the tip was defined by the time t2 for which the valve 25 was set to open during the purging. In this series this time was identical to the time t1 of opening the valve for flushing: t2=t1=1.5 s. By comparing the results presented in FIGS. 2 and 3 one can see that the level of contamination after three cycles of flushing combined with air purging is some 5 times below the level of concentration after cleaning the dispensing tip by comparable quantity of cleaning liquid.

In order to further reduce carryover the invention proposes that the cleaning liquid can be expelled from the dispensing tip while the valve 25 is actuated to flicker between the open and close positions. We explain this result as follows. By actuating the valve we steer the liquid inside the dispensing tip 2 more violently and therefore as a result the contamination is removed more aggressively from the pockets inside the dispensing tip 2. This also applies to dispensers based on other constructions of the solenoid valves.

We have found that general purpose three-way valve can be used for valves 10, 15 and 17. We have found that the valves rated to sustain the pressure difference between inlet and outlet of 6 Bars are generally suitable for many applications in low volume liquid dispensing. In a typical embodiment the valve is specified for the flow rate of 7 liters per minute at a pressure differential of 13.8 psi. As some of the liquids handled by the system can be chemically aggressive, it is beneficial to have the valves with enhanced chemical resistance. A typical valve has the body made of stainless steel and seal of Kalrez. The fitting connections on the valves made of PEEK polymer are usually adequate.

In this embodiment both the vacuum source 7 and the pressure source 6 are sealed off once they are disconnected from the output of the pneumatic source 5. This can be achieved by a particular design of the valve 10 or by installing further valves between the valve 10 and the vacuum and pressure sources. These will be well understood by those skilled in the art and therefore are not shown in FIG. 1. The reason for this is that raising pressure in the flush bottle 20 is relatively time consuming and therefore once the pressure in the flush bottle 20 is established, it is beneficial to maintain it at the constant level throughout the time of the system's operation. Maintaining the constant pressure in the flush bottle 20 will also reduce the power consumption during the system's operation.

The embodiment shown in FIG. 1 is also equipped with the valve 27. The purpose of the valve 27 is to release the pressure from the bottle before the system is powered off or before the flush bottle is refilled. This may be beneficial for safety reasons. For this the valve 27 is switched to the left position and the pressurised gas from the flush bottle 20 can be released through the pathway comprising the outlet 28, the valve 27 and the pressure release outlet 30. The valve 27 could be of the type known as magnetic latching valve but other types of valves are also possible. The benefit of the latching valve is that it only requires power during switching the valve on and off and therefore the valve heats to a lesser extent during the operation. However, it should be noticed that latching valves are bulkier than the conventional valves and also they are more costly and therefore depending on the specific intended application, it may be desirable to avoid using latching valves. Similarly, it may be desirable to release pressure from the pressure source and release negative pressure from the vacuum source before the system is powered off. This could be achieved by switching the valves 27 and 15 both to the left position so that the interior of the pressure source 6 or the vacuum source 7 are open to air through the pressure release outlet 29. The same effect can be achieved by opening the valve 25 with the nozzle of the tip being open to air, then the interior of the pneumatic line is open to air.

Figure 4:
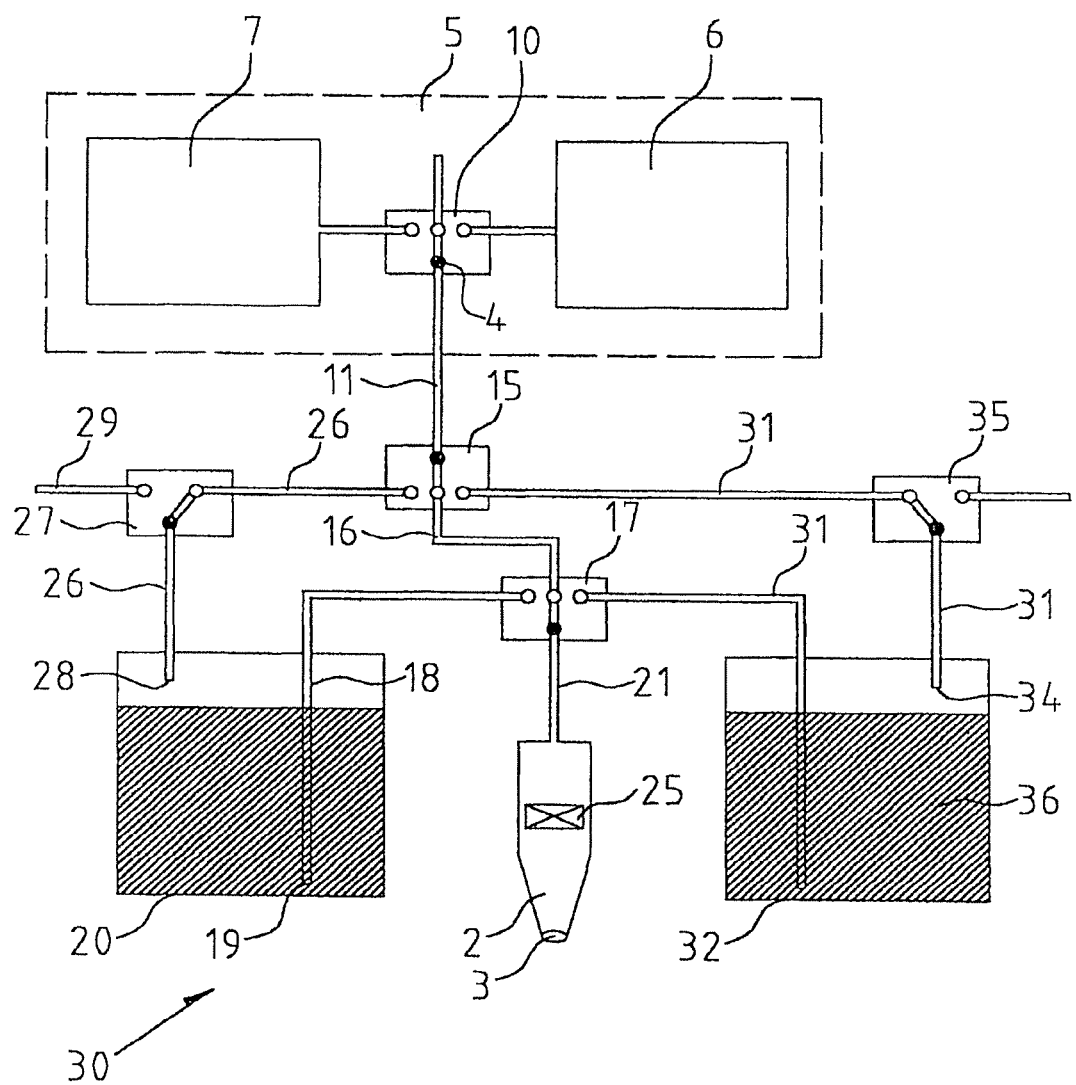
FIG. 4 shows another system for dispensing and aspiration of low volumes of liquids.

FIG. 4 shows another embodiment of the system for dispensing and aspiration of liquids. It is identified by the numeral 30. Parts similar to those described with reference to FIG. 1 are identified by the same reference numerals. Some of the valves are of different construction, however, as they are in the same positions and only have some additional functionality, it is easier for ease of understanding to use the same identifying numerals. It differs from the system shown in FIG. 1 in one respect: it has the third liquid line, namely a bulk sample line 31 that can be connected between the dispensing tip 2 and the pneumatic source 5. In this particular embodiment the bulk sample line 31 can be connected by means of the valves 15 and 17 which in this embodiment are three-position valves. Therefore any one of the three lines: liquid feed line 18, pneumatic line 16 and bulk sample line 31 can be connected between the dispensing tip 2 and the pneumatic source 5 depending on the position of the valves 15 and 17. Those skilled in the art will appreciate that the same effect can be achieved with the help of two-position valves but in this case more than two valves are required instead of two three-position valves 15 and 17. The bulk sample line 31 is coupled to a bulk sample bottle 32 in the manner similar to the coupling of the liquid feed line to the flush bottle 20. Again there is an inlet of the bulk sample line 31 that is coupled into the bulk sample bottle 32 in the air-tight fashion. Then there is an outlet 34 of the bulk sample line that is coupled into the bulk sample bottle 32 also in an air tight fashion. The bulk sample bottle 32 contains bulk sample liquid 36. The bulk sample line can be pressurised by means of the pneumatic source through the inlet of the bulk sample line. The operation of the system is similar to the one described in relation to FIG. 1. The difference is that in addition to the sample liquids aspirated through the nozzle 3 of the dispensing tip 2, further sample liquid, called in this specification bulk sample liquid 36 can be dispensed through the dispensing tip. For this the bulk sample bottle 32 containing the bulk sample liquid needs to be pressurised. The dispensing is achieved by actuating the valve 25. The benefit of this embodiment over the one described in relation to FIG. 1 is that the instrument can be more effectively used for certain applications.

A valve 35 is shown connected to the pressurising line 37. The purpose of this is to release the pressure from the bulk sample bottle 32 for the exchange of liquid or refill in the bulk sample bottle. This is similar to the function of the pressure release valve 27 coupled to the pressurising line 26. Alternatively the valves 27 and 35 can be installed directly to the bulk sample bottle 32 and the flush bottle 20 respectively above the levels of liquids in these bottles. Again the electronics controlling the valves are not shown in FIG. 4. They are preferably controlled by processors coupled to control electronics circuits. These are not shown in FIG. 4 as they are obvious to those skilled in the art.

In situations where a number of sample liquids needs to be transferred between different well plates and then all of them need to be diluted with a buffer liquid, this embodiment may be used. In this case the buffer liquid is placed in the bulk sample bottle. Then the sample liquids are aspirated from the wells and transferred to another well plate. Washing the dispenser is accomplished as described above with reference to FIG. 1. Then the buffer liquid is dispensed from the bulk sample bottle 32 once the valves have connected the bulk sample bottle to the pneumatic source 5. The term bulk sample liquid does not mean that the volume of each dose of dispensing is large. It merely means that the same sample liquid is used to fill many wells and therefore the total volume consumed of such sample liquid is relatively larger than the volume of the samples placed in each well. It should be kept in mind that this volume could still be relatively small. For example, if 20 nl is placed in each well, then the volume of the bulk sample dispensed per 384 well plate is less than 8 μl.

Those skilled in the art will appreciate that the bulk sample line 31 could be connected permanently to the pressure source using a different layout of valves. It should be noticed that a number of dispensing tips may be connected in parallel in a system for dispensing of liquid droplets. In a typical embodiment, 4, 8 or 12 dispensing tips are connected in parallel but another number of dispensing tips can also be used. Typically, all the dispensing tips are identical to each other and in reference to the embodiment of FIG. 4, each of them is equipped with the valve 25. Connecting a number of dispensing tips in parallel is usually done to enhance the productivity of the system so that a number of channels can operate at the same time all dispensing the same bulk sample liquid. Cleaning procedure in this case can be the same as described above if the valves 25 on all the dispensing tips 2 are actuated at the same time or almost simultaneously.

It will be appreciated that while the invention has been described with reference to one particular type of construction of dispensing tip, it can be used with many other dispensing assemblies that are known in the art, such as, for example, those that use positive displacement pumps.

In the embodiment described above, air has been described as being the purging gas, however, it will be appreciated that various other gases may be used such as helium, nitrogen, carbon dioxide and many other inert gases. Ideally, one wants gases that will not go into solution with any of the liquids.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail within the scope of the claims.

The invention claimed is:

1. A method for dispensing one or more liquid droplets from a dispensing assembly and cleaning the dispensing assembly, the method comprising:
   connecting a dispensing tip to a pressure source by at least setting a first switch to a first state, setting a second switch to a second state, and setting a third switch to a third state so as to define a first path between the dispensing tip and the pressure source through at least the first switch, the second switch, and the third switch, the dispensing tip being a part of a dispensing assembly;
   applying a first pressure by the pressure source to a first liquid in the dispensing tip via at least the first path;
   ejecting one or more droplets of the first liquid from the dispensing tip by the applied first pressure, each of the one or more droplets being up to 100 µl in volume;
   connecting the dispensing tip to a first liquid source and the first liquid source to the pressure source, by at least changing the second switch from the second state to a fourth state, changing the third switch from the third state to a fifth state, and setting a fourth switch to a sixth state so as to define a second path between the first liquid source, the pressure source, and the dispensing tip through at least the second switch, the third switch, and the fourth switch, the first liquid source containing a second liquid, the second liquid being different from the first liquid;
   applying a second pressure by the pressure source to the second liquid in the first liquid source via at least the second path;
   delivering at least a portion of the second liquid from the first liquid source to the dispensing tip by the applied second pressure;
   connecting the dispensing tip to the pressure source via at least the first path by at least changing the second switch from the fourth state to the second state and changing the third switch from the fifth state to the third state; and
   expelling at least a part of the portion of the second liquid from the dispensing tip by a purging gas pressurized by the pressure source.

2. The method of claim 1 wherein each of the one or more droplets is up to 50 µl in volume.

3. The method of claim 2 wherein each of the one or more droplets is up to 10 µl in volume.

4. The method of claim 1, and further comprising:
   after the process for ejecting one or more droplets of the first liquid from the dispensing tip by the applied first pressure,
   connecting the dispensing tip to a vacuum source by at least changing the first switch from the first state to a seventh state so as to define a third path between the dispensing tip and the vacuum source via at least the first switch, the second switch, and the third switch; and
   performing an evacuation process to at least the dispensing tip with the vacuum source via at least the third path.

5. The method of claim 1, and further comprising:
   connecting the dispensing tip to a second liquid source and the second liquid source to the pressure source, by at least changing the second switch from the second state to an eighth state, changing the third switch from the third state to a ninth state, and setting a fifth switch to a tenth state so as to define a fourth path between the second liquid source, the pressure source, and the dispensing tip through at least the second switch, the third switch, and the fifth switch, the second liquid source containing a third liquid, the third liquid being different from the first liquid, the third liquid being different from the second liquid;
   applying a third pressure by the pressure source to the third liquid in the second liquid source via at least the fourth path; and
   delivering at least a portion of the third liquid from the second liquid source to the dispensing tip by the applied third pressure via at least the fourth path.

6. The method of claim 1 wherein the process for delivering at least a portion of the second liquid from the first liquid source to the dispensing tip includes delivering a pulsed flow of the second liquid from the first liquid source to the dispensing tip via at least the second path.

7. The method of claim 1 wherein the process for expelling at least a part of the portion of the second liquid from the dispensing tip includes delivering a pulsed flow of the purging gas via at least the first path.

8. The method of claim 1 wherein the purging gas is one selected from a group consisting of air, helium, nitrogen and carbon dioxide.

9. The method of claim 1 wherein the process for expelling at least a part of the portion of the second liquid from the dispensing tip is performed after the process for delivering at least a portion of the second liquid from the first liquid source to the dispensing tip.

* * * * *